(12) United States Patent
Ziejewski

(10) Patent No.: US 6,726,623 B2
(45) Date of Patent: Apr. 27, 2004

(54) BRAIN INJURY DIAGNOSTIC SYSTEM

(76) Inventor: Mariusz Ziejewski, 2363 20th Ave. S., Fargo, ND (US) 58103

( * ) Notice: Subject to any disclaimer, the term of this patent is extended or adjusted under 35 U.S.C. 154(b) by 489 days.

(21) Appl. No.: 09/765,210

(22) Filed: Jan. 17, 2001

(65) Prior Publication Data

US 2002/0028987 A1 Mar. 7, 2002

Related U.S. Application Data

(60) Provisional application No. 60/176,524, filed on Jan. 18, 2000.

(51) Int. Cl.$^7$ .............................. A61B 5/00; A61B 5/04
(52) U.S. Cl. ...................................... 600/300; 600/544
(58) Field of Search ................................ 600/300, 301, 600/378, 544, 545, 546; 340/573.1; 424/2, 570; 434/258

(56) References Cited

U.S. PATENT DOCUMENTS

| | | | | |
|---|---|---|---|---|
| 4,543,957 A | * | 10/1985 | Friedman et al. | 600/300 |
| 5,836,304 A | * | 11/1998 | Kellinger et al. | 128/630 |
| 6,117,073 A | * | 9/2000 | Jones et al. | 600/300 |
| 6,149,586 A | * | 11/2000 | Elkind | 600/300 |
| 6,206,829 B1 | * | 3/2001 | Iliff | 600/300 |
| 6,416,480 B1 | * | 7/2002 | Nenov | 600/557 |
| 6,503,085 B1 | * | 1/2003 | Elkind | 434/236 |

* cited by examiner

Primary Examiner—Daniel Robinson
(74) Attorney, Agent, or Firm—Michael S. Neustel

(57) ABSTRACT

A brain injury diagnostic system for providing a quick and accurate assessment of various accident scenarios for providing an accurate brain injury diagnosis. The invention includes the process of collecting data at the accident site or from an emergency room, entering the collected data into a computer, transferring the collected data to a central computing facility through a communication system, conducting a biomechanical analysis of the collected data at the central computing facility, determining the results of the biomechanical analysis, transferring the results to the computer, and displaying the results upon a computer monitor of the computer preferably prior to the patient's arrival at the emergency room. Based upon the displayed results, health care providers can then make an informed decision regarding the proper treatment for the patient.

19 Claims, 5 Drawing Sheets

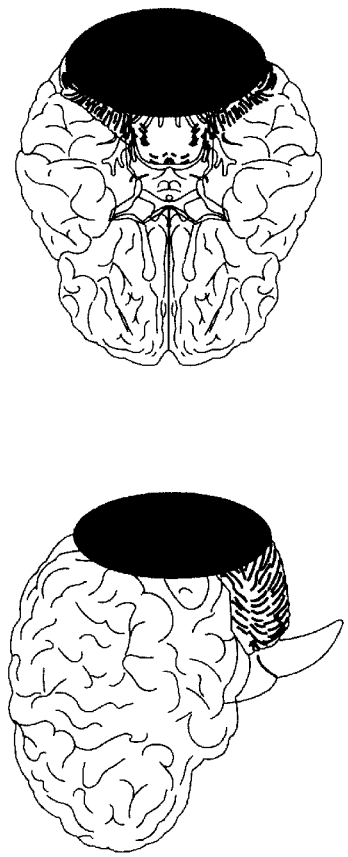

FIG. 6

The biomechanical analysis of Kayla Bowman's body motion indicated that there were two possible scenarios that could have caused the brain injury:
1. The first scenario being an impact against the structure of the semi.
2. The second being an impact with the ground Additional Comments:
Based on studies concerning dynamic fracture forces for cranial bones as reported in SAE J885 standard, the average force necessary for fracture to occur was reported to be approximately 1000 lbs. The minumum forces necessary for skull fracture to occur was reported as 470 lbs. The maximum forces necessary for skull fracture to occur was reported as 1,220 lbs. therefore, the forces acting on Kayla Bowman's head were at least 470lbs.

BRAIN INJURY DIAGNOSTIC SYSTEM

CROSS-REFERENCE TO RELATED U.S. PATENT APPLICATION

I hereby claim benefit under Title 35, United States Code, Section 119(e) of U.S. provisional patent application Ser. No. 60/176,524 filed Jan. 18, 2000. This application is a continuation of the No. 60/176,524 application. The No. 60/176,524 application is currently pending. The No. 60/176,524 application is hereby incorporated by reference into this application.

BACKGROUND OF THE INVENTION

1. Field of the Invention

The present invention relates generally to diagnostic systems and more specifically it relates to a brain injury diagnostic system for providing a quick and accurate assessment of various accident scenarios and an accurate brain injury diagnosis.

Individuals in the medical profession encounter patients that have suffered injuries as a result of vehicle accidents, slip and falls, falling objects and various other scenarios. These individuals often incur mild traumatic brain injury that may not immediately demonstrate any physical symptoms noticeable to the physician or patient.

Traumatic brain injuries are caused by energy being transferred to the individual's head. These forces cause the brain to move. For example, traumatic brain injuries may occur when a contact force is applied directly to the head or when forces are transmitted through the neck without direct contract thereby causing the head to move at a velocity different from the rest of the body. The result of exterior forces upon the head often include stresses applied to the brain and deformation of the brain which can damage the neuronal, vascular, and cytoskeletal structures.

Because often there are no immediate physical symptoms of brain injury, individuals that may have such an injury missed or misdiagnosed by a treating physician. Hence, there is a need for a diagnostic system that allows medical professionals to quickly and accurately assess whether a patient has incurred an injury to the brain so that timely and appropriate treatment for may be provided to the patient.

2. Description of the Prior Art

Brain injury diagnostic tools have been in use for years. Conventional brain injury diagnostic tools are based upon various engineering and medical disciplines which are well-founded and will not be discussed in detail. A well respected source of information regarding the topic of traumatic brain injuries is *Head Trauma Cases: Law and Medicine* (Second Edition, 1997) by Dr. A. C. Roberts which is published by John Wiley & Sons, Inc.

Typically, these diagnostic tools consider the type, direction, magnitude, and duration of force applied to the head. Conventional diagnostic tools also consider regions of the brain affected since different brain regions have different directional sensitivities, structural, and functional tolerances.

The primary problem with conventional brain injury diagnostic tools is that they generally require a lengthy period of time to calculate and make a medical diagnosis. This can be extremely costly to a patient with a traumatic brain injury. In addition, conventional brain injury diagnostic tools require the attending physician to determine whether a traumatic brain injury is present. Often these injuries do not present until hours or days after an accident occurs thereby leading to misdiagnosis. When a patient has incurred a brain injury from forces indirectly applied to the head, such as when the neck forces the head in a different direction, physicians often have no visible sign of injury to the head region and may not pursue the possibility of a traumatic brain injury.

There are numerous medical diagnosis systems and devices that have been attempted to improve upon conventional methods. For example, U.S. Pat. No. 5,704,366 to Tacklind et al.; U.S. Pat. No. 5,687,717 to Halpern et al.; U.S. Pat. No. 5,586,552 to Sakai; U.S. Pat. No. 5,617,871 to Burrows; U.S. Pat. No. 5,715,823 to Wood et al.; U.S. Pat. No. 5,738,102 to Lemelson; U.S. Pat. No. 5,782,878 to Morgan et al.; U.S. Pat. No. 5,899,855 to Brown; U.S. Pat. No. 5,903,211 to Flego et al. all are illustrative of such prior art.

Tacklind et al. (U.S. Pat. No. 5,704,366) discloses a system for monitoring and reporting medical measurements. Tacklind et al. specifically teaches a monitor for storing data records comprising measured values and time stamps and for transmitting the records to a remote reporting unit over a communication system. The remote reporting unit includes a relational database that is updated when records are downloaded from the monitor, a report generator, and a report transmitting unit for transmitting reports to a requesting health care provider.

Halpern et al. (U.S. Pat. No. 5,687,717) discloses a patient monitoring system with chassis mounted or remotely operable modules and portable computer. Halpern et al. specifically teaches at least one chassis, a plurality of patient care modules associated with the chassis, and a portable computer for communicating with and controlling the modules. The chassis continuously polls the module for patient data collected by the module.

While these compositions may be suitable for the particular purpose to which they address, they are not as suitable for providing a quick and accurate assessment of various accident scenarios and an accurate brain injury diagnosis. Conventional brain injury diagnostic devices are extremely time consuming and require the health care provider to first inquire into whether a brain injury has occurred. They typically rely solely upon demonstrable physical symptoms of a brain injury like memory loss or other symptoms.

In this respect, the proposed brain injury diagnostic system departs substantially from the conventional methods of use and compositions of the prior art. In doing so, provides a composition and a method of using the composition primarily developed for the purpose of providing a quick and accurate assessment of various accident scenarios and an accurate brain injury diagnosis.

SUMMARY OF THE INVENTION

In view of the foregoing disadvantages inherent in the known types of medical diagnostic devices and systems present in the prior art, the present invention provides a new brain injury diagnostic system wherein the same can be utilized to provide a quick and accurate assessment of various accident scenarios and an accurate brain injury diagnosis.

The general purpose of the present invention, described subsequently in greater detail, is to provide a new brain injury diagnostic system that has many of the advantages of the medical diagnostic systems mentioned heretofore and many novel features and functions that result in a new brain injury diagnostic system which is not anticipated, rendered obvious, suggested, or even implied by any of the prior art medical diagnostic systems, either alone or in any combination thereof.

To attain this, the present invention generally comprises the process of collecting data at the accident site or from an emergency room, entering the collected data into a computer, transferring the collected data to a central computing facility through a communication system, conducting a biomechanical analysis of the collected data at the central computing facility, determining the results of the biomechanical analysis, transferring the results to the computer, and displaying the results upon a computer monitor of the computer preferably prior to the patient's arrival at the emergency room. Based upon the displayed results, health care providers can then make an informed decision regarding the proper treatment for the patient. The results of a biomechanical analysis may include the probability of brain injury to the patient, 3-dimensional or 2-dimensional animations showing the patient's sequential body motion, a graphical representation of a possible location for any brain injuries, and specific comments concerning the biomechanical analysis. The results of a biomechanical analysis are calculated utilizing well-known biomechanical formulas and algorithms. It can be appreciated that the present invention may be utilized to analyze various other types of bodily injuries beyond brain injuries. The present invention allows for all health care providers around the world to have instant access to results from an accurate biomechanical analysis while within the emergency room thereby allowing them to properly treat the patient. The total number of emergency room computers capable of communicating with the central computing facility is virtually unlimited thereby allowing health care providers at all levels to provide accurate patient evaluations.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a brain injury diagnostic system that will overcome the shortcomings of the prior art.

Another object is to provide a brain injury diagnostic system that provides a quick and accurate assessment of various accident scenarios and an accurate brain injury diagnosis.

An additional object is to provide a brain injury diagnostic system that may be utilized by health care providers in various locations throughout the world.

A further object is to provide a brain injury diagnostic system that provides a central location that quickly determines whether a traumatic brain injury likely occurred to a patient.

Another object is to provide a brain injury diagnostic system that increases the accuracy of the medical diagnosis of a patient with a traumatic brain injury.

An additional object is to provide a brain injury diagnostic system that provides a diagnosis based upon data collected immediately at the accident site or directly from an emergency room.

A further object is to provide a brain injury diagnostic system that instantly displays the diagnostic results in an easy to understand format for an attending physician.

Another object is to provide a brain injury diagnostic system that can be utilized by any health care provider 24 hours a day.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific use illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

FIG. 6 is a second sample display of the brain injury diagnosis results.

DESCRIPTION OF THE PREFERRED EMBODIMENT

Figure 1:
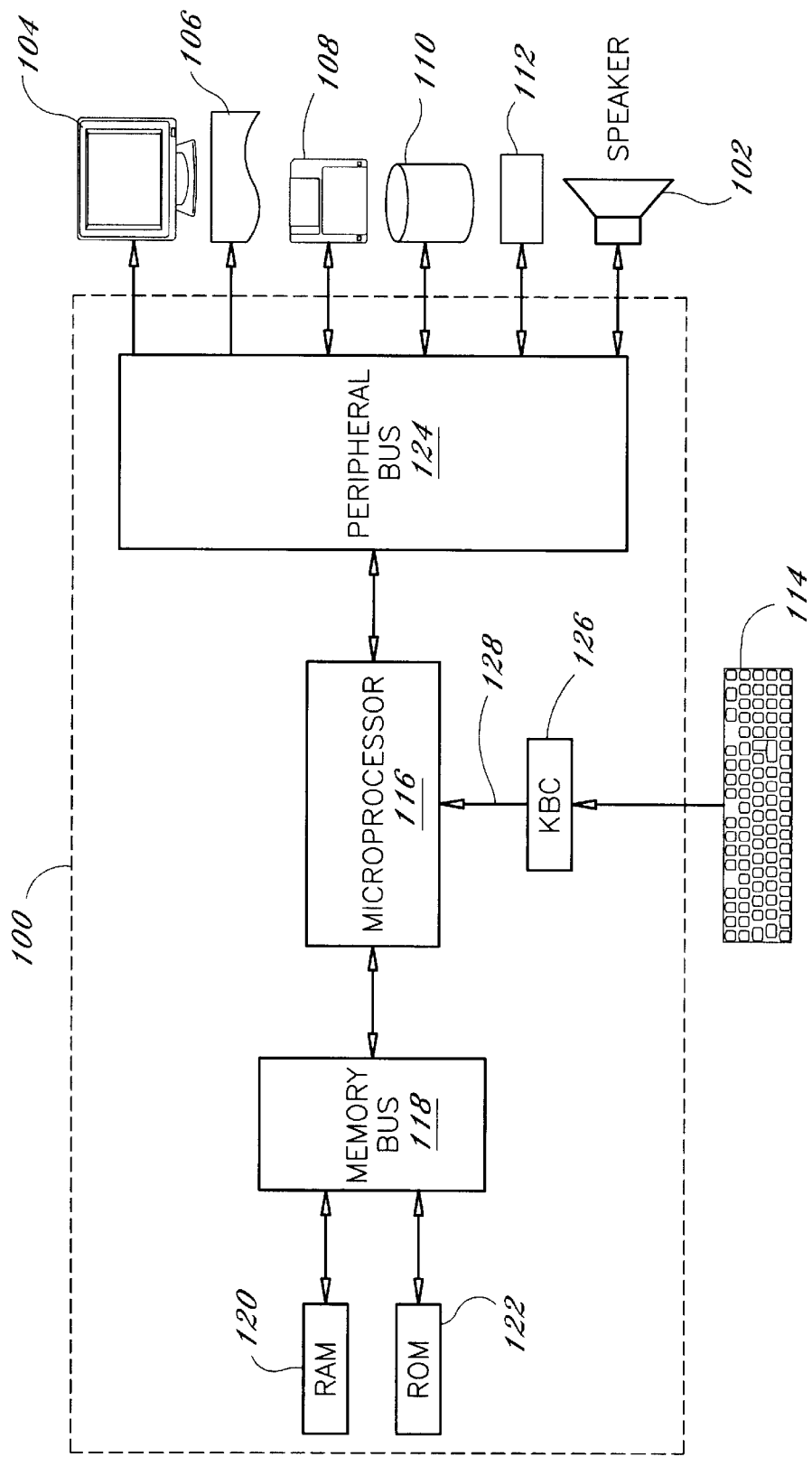
FIG. 1 is a box diagram of an exemplary computer system utilized to execute the present invention.

Turning now descriptively to the drawings, in which similar reference characters denote similar elements throughout the several view, FIGS. 1 through 6 illustrate a brain injury diagnostic system 10, which comprises the process of collecting data at the accident site or from an emergency room, entering the collected data into a computer, transferring the collected data to a central computing facility through a communication system, conducting a biomechanical analysis of the collected data at the central computing facility, determining the results of the biomechanical analysis, transferring the results to the computer, and displaying the results upon a computer monitor of the computer preferably prior to the patient's arrival at the emergency room. Based upon the displayed results, health care providers can then make an informed decision regarding the proper treatment for the patient. The results of a biomechanical analysis may include the probability of brain injury to the patient, 3-dimensional or 2-dimensional animations showing the patient's sequential body motion, a graphical representation of a possible location for any brain injuries, and specific comments concerning the biomechanical analysis. The results of a biomechanical analysis are calculated utilizing well-known biomechanical formulas and algorithms. It can be appreciated that the present invention may be utilized to analyze various other types of bodily injuries beyond brain injuries. The present invention allows for all health care providers around the world to have instant access to results from an accurate biomechanical analysis while within the emergency room thereby allowing them to properly treat the patient. The total number of emergency room computers capable of communicating with the central computing facility is virtually unlimited thereby allowing health care providers at all levels to provide accurate patient evaluations. The above process will now be described in greater detail.

Exemplary Computer System

Figure 2:
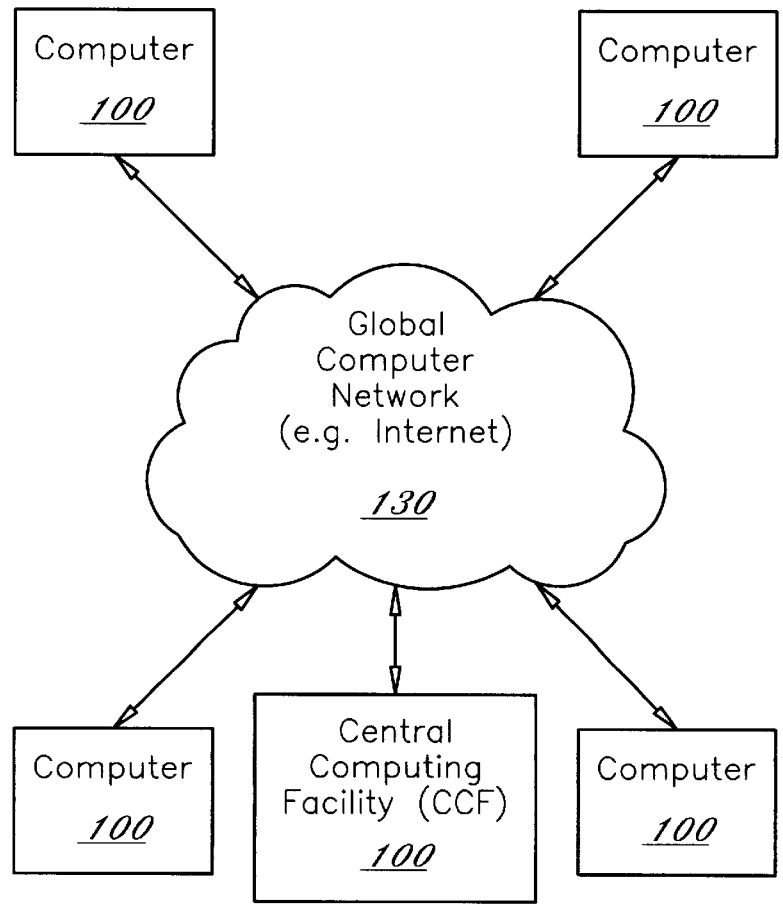
FIG. 2 is a block diagram illustrating an exemplary communication channel between a searcher computer system and database.
Figure 3:
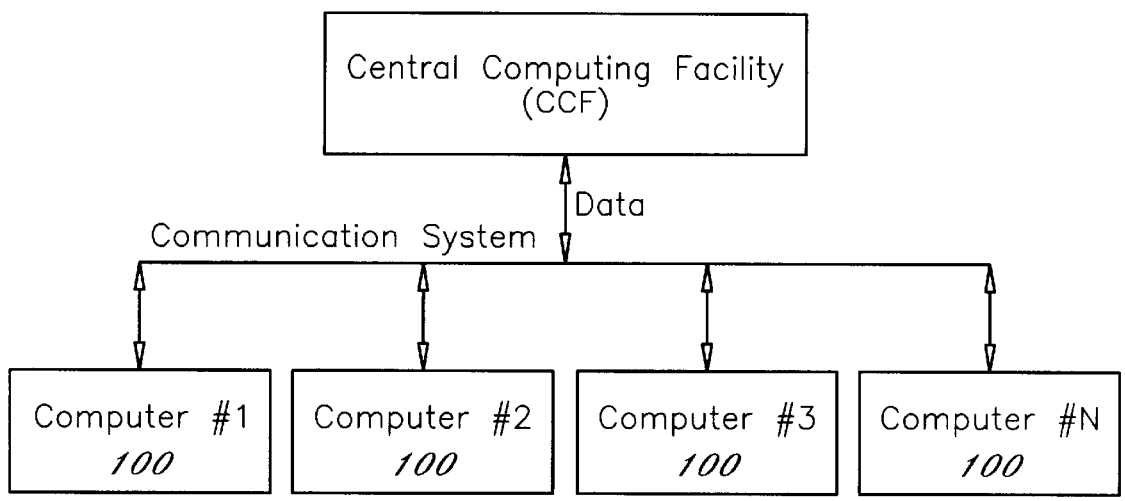
FIG. 3 is a flowchart of the present invention.
Figure 4:
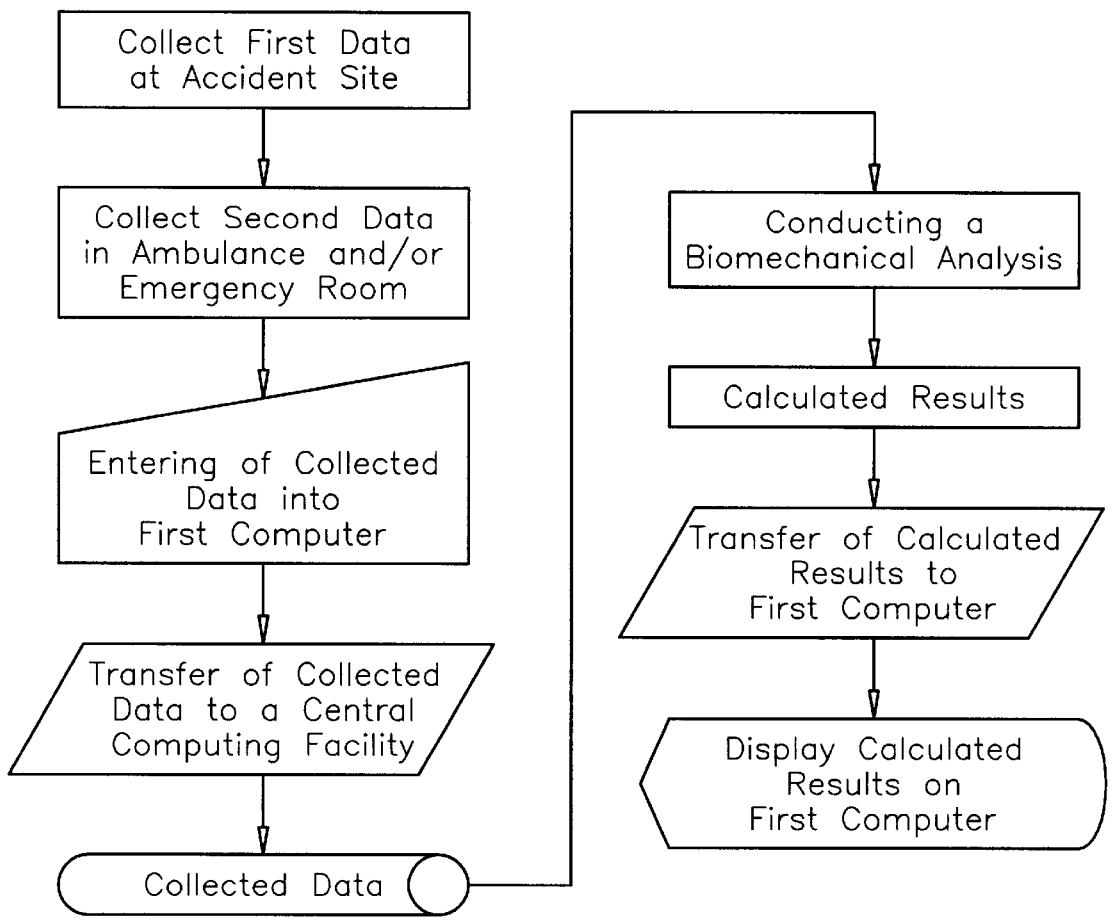
FIG. 4 is a block diagram illustrating the connections and communications between various emergency room computers and the central computing facility.

The present invention is preferably operated upon a global computer network such as the Internet 130. As shown in FIG. 2, the Internet 130 is comprised of a "global computer network". Wherein a plurality of computer systems 100 around the world are in communication with one another via this global computer network. The present invention preferably utilizes the Internet 130, however it can be appreciated that as future technologies are created that various aspects of the invention may be practiced with these improved technologies. More particularly, wireless technologies provide a suitable medium for operating the present invention.

FIG. 1 is a block diagram of an exemplary computer system 100 for practicing the various aspects of the present invention. Computer system 100 includes a display screen (or monitor) 104, a printer 106, a floppy disk drive 108, a hard disk drive 110, a network interface 112, and a keyboard 114. Computer system 100 includes a microprocessor 116, a memory bus 118, random access memory (RAM) 120, read only memory (ROM) 122, a peripheral bus 124, and a keyboard controller 126. Computer system 100 can be a personal computer (such as an APPLE computer, an IBM computer, or one of the compatibles thereof), a workstation computer (such as a SUN MICROSYSTEMS or HEWLETT-PACKARD workstation), or various other types of computers.

The microprocessor 116 is a general purpose digital processor which controls the operation of the computer system 100. Microprocessor 116 can be a single-chip processor or implemented with multiple components. Using instructions retrieved from memory, microprocessor 116 controls the reception and manipulations of input data and the output and display of data on output devices.

Memory bus 118 is used by microprocessor 116 to access RAM 120 and ROM 122. RAM 120 is used by microprocessor 116 as a general storage area and as scratch-pad memory, and can also be used to store input data and processed data. ROM 122 can be used to store instructions or program code followed by microprocessor 116 as well as other data.

Peripheral bus 124 is used to access the input, output and storage devices used by the computer system 100. In the described embodiment(s), these devices include a display screen 104, a printer device 106, a floppy disk drive 108, a hard disk drive 110, and a network interface 112. A keyboard controller 126 is used to receive input from the keyboard 114 and send decoded symbols for each pressed key to microprocessor 116 over bus 128.

The display screen 104 is an output device that displays images of data provided by the microprocessor 116 via the peripheral bus 124 or provided by other components in the computer system 100. The printer device 106 when operating as a printer provides an image on a sheet of paper or a similar surface. Other output devices such as a plotter, typesetter, etc. can be utilized in place of, or in addition to, the printer device 106.

The floppy disk drive 108 and the hard disk drive 110 can be utilized to store various types of data. The floppy disk drive 108 facilitates transporting such data to other computer systems, and the hard disk drive 110 permits fast access to large amounts of stored data.

The microprocessor 116 together with an operating system operate to execute computer code and produce and use data. The computer code and data may reside on RAM 120, ROM 122, or hard disk drive 120. The computer code and data could also reside on a removable program medium and loaded or installed onto computer system 100 when needed. Removable program mediums include, for example, CD-ROM, PC-CARD, floppy disk and magnetic tape.

The network interface circuit 112 is utilized to send and receive data over a network connected to other computer systems. An interface card or similar device and appropriate software implemented by microprocessor 116 can be utilized to connect the computer system 100 to an existing network and transfer data according to standard protocols.

The keyboard 114 is used by a user to input commands and other instructions to the computer system 100. Other types of user input devices can also be used in conjunction with the present invention. Other types of user input devices can also be utilized in conjunction with the present invention. For example, pointing devices such as a computer mouse, a track ball, a stylus, or a tablet to manipulate a pointer on a screen of the computer system 100.

The present invention can also be embodied as computer readable code on a computer readable medium. The computer readable medium is any data storage device that can store data which can be thereafter be read by a computer system. Examples of the computer readable medium include read-only memory, random-access memory, magnetic data storage devices such as diskettes, and optical data storage devices such as CD-ROMs. The computer readable medium can also be distributed over a network coupled computer systems so that the computer readable code is stored and executed in a distributed fashion.

Exemplary Communication System

The present invention is preferably operated upon a global computer network such as the Internet 130. As shown in FIG. 2, the Internet 130 is comprised of a "global computer network". Wherein a plurality of computer systems 100 around the world are in communication with one another via this global computer network. The present invention preferably utilizes the Internet 130, however it can be appreciated that as future technologies are created that various aspects of the invention may be practiced with these improved technologies. More particularly, wireless technologies provide a suitable medium for operating the present invention.

Step #1. Data Acquisition

Immediately after a vehicle accident occurs, paramedics or other trained professionals will inquire about the extent of the vehicle damage as the patient is being cared for. It can be appreciated that accidents include vehicle, slip and falls, falling objects and others that cause bodily damage.

The data acquired will include statements from the victim and witnesses as to what occurred to the patient. For accidents involving vehicles, pictures are taken of the damaged vehicles preferably with a digital camera that is capable of storing one or more digital image files. The image files are stored or transferred upon a conventional storage medium such as a 3½ inch computer disk, e-mail or other communication means. The photographs preferably are taken from two specified locations that allow the analysis software to make an accurate analysis of the accident. The required data is not time consuming hence the data acquisition will not interfere with the care provided to the patient.

Prior to the patient's arrival at the emergency room, the image files and collected data will be electronically uploaded to the central computing facility. While the patient is in the ambulance, the attending EMT may acquire further data from the patient regarding the accident and potential injuries.

Step 2. Data Entry

After the collected data is acquired either immediately at the scene of the accident or directly in the emergency room, the collected data is entered into a computer within the ambulance or directly from the emergency room. The collected data includes personal information regarding the patient, the image files, accident data, and any other relevant data.

The data is entered using a data entry software program. The collected data provides the foundation for a detailed biomechanical analysis and assessment of the severity of the accident and likelihood of brain injury. The collected data is temporarily stored upon the computer after entered.

Step 3. Collected Data Transferred to Central Computing Facility

After the collected data is entered into the computer, the collected data is then transferred to a central computing facility (CCF) through a communications system. The central computing facility is comprised of at least one computer programmed to analyze the collected data in a biomechanical analysis. The at least one computer utilized as a central computing facility may be comprised of any known computer architecture and system.

A suitable communications system for the collected data to be transferred upon is the Internet. Other suitable communications systems include satellite communications, radio signal, or direct telephone connection. It can be appreciated that various other well-known communication systems may be utilized for transferring the collected data to the central computing facility.

Step 4. Analysis of Collected Data

After the collected data is transferred to the central computing facility, the central computing facility analyzes the collected data utilizing well established formulas, algorithms and theories to determine whether a brain injury is likely and if so the probable extent of the injury. Since there are numerous authorities on how to determine traumatic brain injury, only a few will be referenced in this application.

This application incorporates by reference all information published within *Head Trauma Cases: Law and Medicine* (Second Edition, 1997) by Dr. A. C. Roberts which is published by John Wiley & Sons, Inc. This application also incorporates by reference all information published within *Traumatic Brain Injury: Bioscience and Mechanics*, "On the Mechanics of Impact Neurotrama: A Review and Critical Synthesis," 1996, Bandak. This application also incorporates by reference all information published within *Experimental Neurology*, "Distribution of Forebrain Diffuse Axonal Injury Following Inertial Closed Head Injury in Miniature Swine," 1994 (126: 291–299), D. T. Ross. This application also incorporates by reference *Journal of Biomechanics*, "Physical Model Simulations of Brain Injury in the Primate," 1990, Thibault et al. This application also incorporates by reference all other material published as of the date of the filing of the application relating to bodily injury which are generally well known in the art.

The central computing facility will analyze the collected data using a biomechanical analysis. The biomechanical analysis can be separated into four different categories: (i) impact environment analysis, (ii) total human body dynamics analysis, (iii) human brain dynamics analysis, and (iv) human brain tolerance comparison. Utilizing these four categories of analysis, an accurate determination can be made of the patient's injuries including traumatic brain injury.

A. Impact Environment Analysis

Impact environment analysis is designed to evaluate the physical environment surrounding a patient at the moment of the injury causing event. Information considered for the impact environment analysis includes information describing the environment such as the weight and shape of a falling object, the height an object fell, surface characteristics for direct impact events, and the specifics of an acceleration/deceleration event. For example, when the environment is moving relative to the patient (falling object and vehicular collisions), engineering analysis is a necessary part of the evaluation to determine the external forces applied to the patient's body.

For vehicle crashes a public domain software program entitled CRASH3 is preferably utilized to analyze the accident. The content of the manuals and the software for CRASH3 are incorporated by reference into this application. It can be appreciated that there are various other software programs that may be utilized to simulate a vehicle accident. CRASH3 reconstructs single and two vehicle accidents and is based upon the Calspan Reconstruction of Accident Speeds on the Highway (CRASH). CRASH3 also includes refinements and enhancements provided by the National Highway Traffic Safety Administration (NHTSA) and Engineering Dynamics Corporation. CRASH3 determines the conditions of impact, including the impact velocities and delta-V (speed change) of the vehicles, using the above stated collected data. The minimum collected data to operate CRASH3 is a description of the vehicle damage. The results generated by CRASH3 is the assessment of the severity of impact expressed in terms of delta-V and magnitude and principal direction of force. CRASH3 also displays the calculated results in a graphical form which display the location and shape of the vehicle damage including a close-up view of the vehicles at the moment of impact.

B. Total Human Body Dynamics Analysis

The total human body dynamics analysis is for determining the involuntary response of the patient's body to its environment and the consequent forces and accelerations of the patient's body. The total human body dynamics analysis will preferably be completed utilizing a well-known public domain software program entitled ATB (Articulated Total Body computer program) designed to predict human body dynamics during automobile accidents, aircraft crashes, aircraft ejection, and other potentially hazardous events. The ATB program is a three-dimensional, rigid body dynamics program based on the Crash Victim Simulator developed by NHTSA during the early 1970's. The ATB program is capable of predicting the motion of the human body and its interaction with objects within a vehicle such as seats. The ATB program is also capable of providing information such as the forces within the patient's body during the moment of impact. To perform the analysis with the ATB program, a computer model of the patient's body must first be generated which can be accomplished with a public domain program called GEBOD which is designed to generate ATB model input data. GEBOD utilizes a set of 32 body dimensions to compute the joint center locations, segment sizes, masses, and principal moments of inertia. It can be appreciated that various other computer programs may be utilized to accomplish the above.

C. Human Brain Dynamics Analysis

Human brain dynamics analysis determines the magnitude and location of internal forces acting upon the brain during impact. For the human brain dynamics analysis to properly calculate internal forces, it is necessary to utilize sophisticated finite element computer programs to determine the motion and deformation of the brain during impact. The human brain dynamics analysis preferably utilizes an elliptical brain model developed by individuals at North Dakota State University (see Appendix 2 for more information).

D. Human Brain Tolerance Comparison

The human brain tolerance comparison is utilized to asses the effect of the internal forces within the brain during the moment of impact. During the human brain tolerance comparison, results from either the total human body dynamics analysis or the human brain dynamics analysis are compared to published human brain tolerances for the specific type of force applied.

The effect of external forces on the patient's brain are thoroughly assessed utilizing existing methods of biomechanical evaluation wherein there are four different ways the biomechanical evaluation can be performed: linear acceleration of head, angular acceleration of head, combined linear and angular acceleration, and extent of brain tissue stretching. Although all four of these analysis may be utilized, the health care provider will receive a probability chart based upon the analysis that yields the highest probability for brain injury. If a significant discrepancy exists between the various equivalent analyses, the health care provider will be notified and all of the results will be posted to the health care provider. The results of the human brain tolerance comparison indicate the probability and severity of brain injury.

Step 5. Results Transferred to Emergency Room Computer

After the above analysis has been performed by the central computer facility, the results of the analysis are transferred to the emergency room computer through the communications system. A suitable communications system has been discussed previously.

Step 6. Displaying Results

Figure 5:
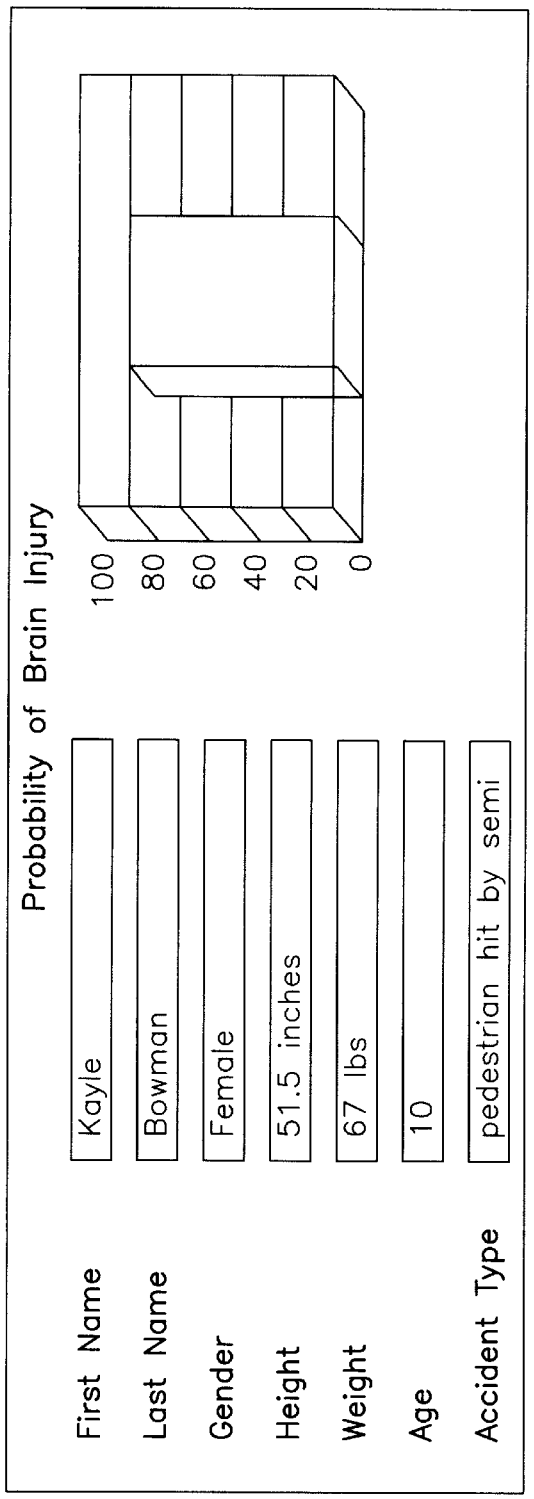
FIG. 5 is a first sample display of the brain injury diagnosis results.
Figure 5:
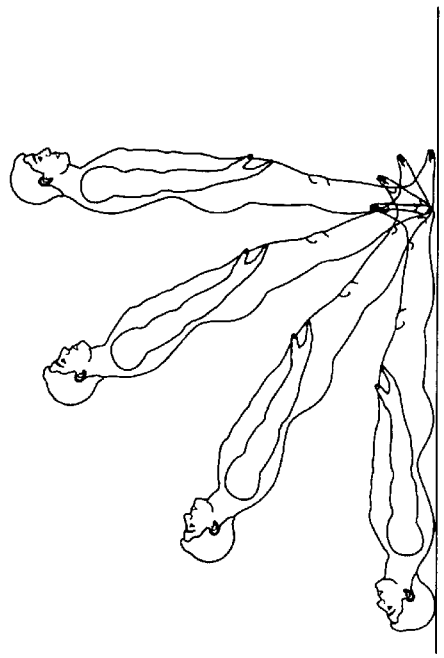

After the results of the biomechanical analysis have been transferred from the central computer facility to the computer within the emergency room, the computer displays the results in an easy to understand format as illustrated in FIGS. 5 and 6 of the drawings. The results will include information such as identification of the case, the probability of brain injury, animations showing the patient's sequential body motion, a picture of the possible location for brain injury, and specific comments concerning the biomechanical analysis. The health care provider then will have the option to select an additional view to gain a better understanding of the patient's body motion during the accident. The results of the biomechanical analysis will be displayed in both a textual and graphical format upon the computer.

As to a further discussion of the manner of usage of the present invention, the same should be apparent from the above description. Accordingly, no further discussion relating to the manner of usage will be provided.

With respect to the above description then, it is to be realized that the optimum relationships for the components of the invention, to include variations in proportions and manner of use are deemed readily apparent and obvious to one skilled in the art.

Therefore, the foregoing is considered as illustrative only of the principles of the invention. Further, since numerous modifications and changes will readily occur to those skilled in the art, it is not desired to limit the invention to the exact composition and use shown and described, and accordingly, all suitable modifications and equivalents may be resorted to, falling within the scope of the invention.

I claim:

1. A brain injury diagnostic system for providing a brain injury diagnosis prior to admission of a patient to an emergency room based upon data accumulated from an accident site, comprising the steps of:
   (a) acquiring accident data performed at least at the accident site and within an emergency-transporting vehicle, wherein said accident data includes accident site information, patient information and physical environment information;
   (b) entering said accident data into a first computer;
   (c) transferring said accident data from said first computer to a central computing facility;
   (d) analyzing said accident data based upon an impact environment analysis, a total human body dynamics analysis, a human brain dynamics analysis, and a human brain tolerance comparison;
   (e) developing a brain injury diagnosis based upon said accident data;
   (f) transferring said brain injury diagnosis to a second computer located within the emergency room; and
   (g) displaying said result upon said second computer.

2. The brain injury diagnostic system of claim 1, wherein said human brain tolerance comparison is performed utilizing a linear acceleration of the head analysis.

3. The brain injury diagnostic system of claim 1, wherein said human brain tolerance comparison is performed utilizing an angular acceleration of the head analysis.

4. The brain injury diagnostic system of claim 1, wherein said brain injury diagnosis includes a probability of brain injury result.

5. The brain injury diagnostic system of claim 1, wherein said brain injury diagnosis includes a visual display of a possible location of brain injury.

6. The brain injury diagnostic system of claim 5, wherein said brain injury diagnosis includes a three-dimensional simulation of the accident.

7. The brain injury diagnostic system of claim 6, wherein said brain injury diagnosis includes comments regarding said brain injury diagnosis.

8. A brain injury diagnostic system for providing a brain injury diagnosis prior to admission of a patient to an emergency room based upon data accumulated from an accident site, comprising the steps of:
   (a) acquiring accident data performed at least at the accident site and within an emergency-transporting vehicle, wherein said accident data includes accident site information, patient information and physical environment information;
   (b) entering said accident data into a first computer;
   (c) transferring said accident data from said first computer to a central computing facility;
   (d) analyzing said accident data;
   (e) developing a brain injury diagnosis based upon said accident data;
   (f) transferring said brain injury diagnosis to a second computer located within the emergency room; and
   wherein said step of analyzing said accident data is based upon an impact environment analysis, a total human body dynamics analysis, a human brain dynamics analysis, and a human brain tolerance comparison.

9. The brain injury diagnostic system of claim 8, wherein said human brain tolerance comparison is performed utilizing a linear acceleration of the head analysis.

10. The brain injury diagnostic system of claim 9, wherein said human brain tolerance comparison is performed utilizing an angular acceleration of the head analysis.

11. The brain injury diagnostic system of claim 10, wherein said brain injury diagnosis includes a probability of brain injury result.

12. The brain injury diagnostic system of claim 11, wherein said brain injury diagnosis includes a visual display of a possible location of brain injury and a three-dimensional simulation of the accident.

13. A brain injury diagnostic system for providing a brain injury diagnosis prior to admission of a patient to an emergency room based upon data accumulated from an accident site, comprising the steps of:

(a) acquiring accident data;

(b) entering said accident data into a first computer;

(c) transferring said accident data from said first computer to a central computing facility;

(d) analyzing said accident data based upon at least one analysis selected from a group consisting of an impact environment analysis, a total human body dynamics analysis, a human brain dynamics analysis, and a human brain tolerance comparison; and (e) developing a brain injury diagnosis based upon said accident data.

14. The brain injury diagnostic system of claim 13, including the step of transferring said brain injury diagnosis to a second computer located within the emergency room.

15. The brain injury diagnostic system of claim 13, including the step of displaying said result upon said second computer.

16. The brain injury diagnostic system of claim 13, wherein said step of acquiring accident data is performed at the accident site and within an emergency-transporting vehicle.

17. The brain injury diagnostic system of claim 13, wherein said accident data includes accident site information, patient information and physical environment information.

18. The brain injury diagnostic system of claim 13, wherein said human brain tolerance comparison is performed utilizing a linear acceleration of the head analysis.

19. The brain injury diagnostic system of claim 13, wherein said human brain tolerance comparison is performed utilizing an angular acceleration of the head analysis.

* * * * *